United States Patent [19]

Jurewicz

[11] 3,996,274
[45] Dec. 7, 1976

[54] METHOD FOR PRODUCING CHLOROBENZOYL CHLORIDE

[75] Inventor: Anthony T. Jurewicz, Kendall Park, N.J.

[73] Assignee: Mobil Oil Corporation, New York, N.Y.

[22] Filed: Nov. 22, 1974

[21] Appl. No.: 526,288

[52] U.S. Cl. .......................................... 260/544 D
[51] Int. Cl.² ...................................... C07C 51/58
[58] Field of Search ................... 260/544 D, 544 M

[56] References Cited
UNITED STATES PATENTS 2,890,243  6/1959  Brown et al. .............. 260/544 D X
3,816,526  6/1974  Jurewicz ...................... 260/544 M

*Primary Examiner*—O
*Assistant Examiner*—Ethel G. Love
*Attorney, Agent, or Firm*—Charles A. Huggett; Howard M. Flournoy

[57] ABSTRACT

Chlorination of benzoyl chloride at controlled temperatures in the presence of a ferric halide-iodine cocatalyst system, and in the absence of solvent provides higher yields of the meta-isomer of monochlorobenzoyl chloride than is obtained when a single catalyst such as, e.g. $FeCl_3$ only is used.

4 Claims, No Drawings

METHOD FOR PRODUCING CHLOROBENZOYL CHLORIDE

BACKGROUND OF THE INVENTION

1. Field of the Invention

This invention is directed to a process of making meta-chlorobenzoyl chloride in improved yields. Meta-chlorobenzoyl chloride is a highly useful starting material in the production of certain herbicides, i.e. halophenoxy nitrobenzoates. The process of this invention, therefore, can be utilized in making the halophenoxybenzoic acid herbicides disclosed by U.S. Pat. No. 3,652,645.

2. Description of the Prior Art

E. Hope and G. C. Reily reported, in the Journal of the Chemical Society, Vol. 121, page 2,510, 1922, the chlorination of benzoyl chloride. However, no solvents were used and the catalyst consisted of ferric chloride only, i.e. benzoyl chloride was chlorinated with anhydrous ferric chloride as the only catalyst. The yield of monochlorobenzoyl chlorides was 76% at 87% benzoyl chloride conversion. The isomer distribution of the monochlorinated fraction was 83.5% meta-, 14.5% ortho- and 2% para-chlorobenzoyl chloride.

Other methods that have been described in the prior art for the preparation of this chloride generally start with materials that already contain nuclear chloride, as for example, the conversion of chlorobenzaldlhyde to monochlorobenzoyl chloride using carbon tetrachloride as solvent. In such processes, the monochlorinated form produced contain meta and disproportionate amounts of ortho- and para-fractions.

U.S. Pat. No. 3,816,526 shows improvement in the chlorination of benzoyl chloride when the reaction is carried out in a chlorinated hydrocarbon solvent; the improvement being selectivity to meta-chlorobenzoyl chloride. For example, at 85% benzoyl chloride conversion, 80% monochlorobenzoyl chlorides and 5% dichlorobenzoyl chlorides were obtained. The isomer distribution of the monochlorinated fraction was 91.5% meta-, 6.5% ortho-, and 2% para-chlorobenzoyl chlorides.

U.S. Pat. No. 2,890,243 discloses preparation of polychlorobenzoic acids by chlorinating benzoyl chloride at temperatures from 100°–150° C or higher in the presence of ferric chlorideiodine catalyst and in the absence of a solvent to produce a mixture of polychlorobenzoyl chloride.

Applicant, however, has discovered a catalytic process wherein the desired meta-isomer of monochlorobenzoyl chloride is preferentially obtained in high yield without the use of high temperatures or solvent.

SUMMARY OF THE INVENTION

This invention provides, in a method for producing monochlorobenzoyl chloride, the improvement whereby benzoylchloride is chlorinated at relatively low temperatures, i.e. less than 50° C in the presence of a ferric halide-iodine cocatalyst system without the use of a solvent thereby producing the desired metaisomer in higher yield than when for example $FeCl_3$ alone is used as the catalyst.

DESCRIPTION OF SPECIFIC EMBODIMENTS

This invention, therefore, is directed to a process for synthesizing mono-chlorobenzoyl chloride in which the desired meta-isomer of a monochlorinated fraction of said chloride is preferentially produced in high yield. Accordingly, applicant's process produces higher yields, with the added benefit of not using a solvent or high temperatures, of the desired meta-isomer than the above-referred to prior art methods, using a ferric chloride catalyst system.

This invention is specifically directed towards the neat mono-chlorination of benzoylchloride in the presence of an anhydrous ferric chloride-iodine cocatalyst system at low temperatures in the absence of a solvent. The combination of the cocatalysts, i.e., ferric chloride and iodide and the reaction temperatures disclosed herein apparently result in greater selectivity to the meta-isomer.

As alluded to above, there are several advantages of the neat chlorination of benzoyl chloride using the $FeCl_3$—$I_2$ cocatalyst system over that done in the above disclosed prior art processes: e.g., (1) approximately three times as much benzoyl chloride can be reacted/batched in a given reactor volume, (2) the purification system is simplified since no solvent stripping operation is required and (3) the cost and inherent problems of maintaining a high temperature reaction zone are eliminated.

The concentration of the $FeCl_3$ can vary from about 0.1 to about 5 weight % based on the amount of benzoyl chloride present, with the preferred range being from about 0.2 to 3 wt. %. The weight ratio of ferric chloride to iodine can vary from about 1–75; preferred ratio is from about 5–50. Reaction temperature, however, must be carefully controlled within the limits of from about 0° to 50° C. The preferred temperature range is from about 5°–35° C. The rate of chlorine addition can be varied, interalia, to suit the equipment being used. The process can take place at atmospheric pressure or, at any convenient or desired pressure.

A review of prior art (excluding U.S. Pat. No. 3,816,526) reveals that the best overall yield of monohalobenzoyl halides is approximately 76% with isomer distribution of the monohalogenated fraction yielding about 83% of the meta-fraction. Utilizing applicant's invention over 85% of the benzoyl halide is converted to the mono-chlorinated form with up to about 95% of said mono-chlorinated fraction being meta and unlike U.S. Pat. No. 3,816,526 no solvent is required.

The following detailed examples are intended as illustrations rather than limitations on the scope of this invention so as to provide a better understanding of the nature, objects and advantages of the invention.

EXAMPLE 1

A four neck flask was charged with 280g of benzoyl chloride, 4g of anhydrous ferric chloride and 0.3g iodine. Chlorine was bubbled through the solution at 280ml/min. After 150 minutes at a temperature of 35° C, 79% of the benzoyl chloride was chlorinated to 67.4% of the monochlorinated and 11.7% of the dichlorinated product. The isomer ratio of the monochlorinated material was ortho 8.4%, meta 89.8% and para 1.7%.

EXAMPLE 2

For comparison, a run was made under conditions identical to Example 1 except for the absence of iodine. After 180 minutes 82% of the benzoyl chloride was converted to 73% monochlorobenzoyl chlorides and 9% dichlorobenzoyl chlorides. The isomer distribution of the monochlorinated material was respectively ortho/meta/para 14.3/83.7/2%.

A comparison of Example 1 and 2 shows the claimed improvement in selectivity to the meta isomer when cocatalyst $FeCl_3—I_2$ is employed, i.e. the cocatalyt system of this invention as opposed to $FeCl_3$ alone.

EXAMPLE 3

Under conditions identical to Example 1 except that the temperature was held at 20° C with cooling a comparison run was made. After 150 minutes, 87% of the benzoyl chloride was converted to 71.5% monochlorobenzoyl chlorides and 15.5% dichlorobenzoyl chlorides. The isomer distribution of the monochlorinated material was respectively ortho/meta/para 5.5/93/1.5%.

EXAMPLE 4

A run was made under identical conditions to Example 1 except that the temperature was kept at 10° C with cooling. After 150 minutes, 87% of the benzoyl chloride was converted to 72% monochlorobenzoyl chlorides and 15% dichlorobenzoyl chlorides. The isomer distribution of the monochlorinated material was ortho/meta/para 5/94/1% respectively.

EXAMPLE 5

140g of benzoyl chloride, 0.1g $I_2$ and 1.0g of iron powder were charged to a four neck flask. Chlorine was bubbled through the solution at 140 ml/min. After 240 minutes at 25°–30° C, 79% of the benzoyl chloride was converted to 67% monochlorobenzoyl chlorides and 12% dichlorobenzoyl chlorides. The isomer distribution of the monochlorinated material was ortho/meta/para 3.8/94.4/1.8% respectively.

EXAMPLE 6

For purposes of comparison, a run was made under similar conditions but at a temperture (elevated) outside the scope of this application. A four neck flask was charged with 280g benzoyl chloride, 4g anhydrous ferric chloride and 0.3g iodine. Chlorine was bubbled through the solution at 400 ml/min. After 120 minutes at a temperature of 94° C, 80% of the benzoyl chloride was chlorinated to 66% of the monochlorinated and 14% of the dichlorinated product. The isomer distribution of the monochlorinated material was respectively ortho/meta/para 12.8/84.6/2.6.

A comparison of Examples 1, 3, 4 and 5 show the claimed improvement, i.e., yields of from 89.8–94.4% of the meta isomer of the monochlorinated fraction as opposed to only 84.6% when an elevated temperature is used.

The examples clearly demonstrate the advantages of using applicant's ferric halide-iodine cocatalyst system; low temperatures (0°–50° C), the absence of solvents to give higher yields of the meta-isomer of monochlorinated benzoylchloride than when high temperatures or only $FeCl_3$ catalyst is used.

Although the present invention has been particularly described with respect to preferred embodiments, all the disclosed embodiments and modifications apparent to one ordinarily skilled in the art are considered to be within the scope of this invention.

What is claimed is:
1. In a method for producing monochlorobenzoyl chloride the improvement wherein benzoyl chloride is chlorinated in the absence of a solvent and in the presence of an anhydrous ferric chloride-iodine cocatalyst system at a temperature of from about 0°–50° C. in which the concentration of the ferric chloride is from about 0.1–5 weight % based on the weight of the benzoyl chloride and the weight ratio of ferric chloride to iodine is from about 1–75.

2. The method of claim 1 wherein the chlorination is carried out at a temperature of from about 5° to about 35° C.

3. The method of claim 1 wherein the monochlorobenzoyl chloride is meta-chlorobenzoyl chloride.

4. The method of claim 1 wherein the concentration of $FeCl_3$ is from about 0.2 to about 3% weight based on the amount of benzoylchloride present and the weight ratio of $FeCl_3$ to $I_2$ is about 5–50.

* * * * *